(12) United States Patent
Walker

(10) Patent No.: US 10,675,419 B2
(45) Date of Patent: Jun. 9, 2020

(54) DECONGESTING DEVICE FOR INFANTS

(71) Applicant: Lizbeth Walker, Kissimmee, FL (US)

(72) Inventor: Lizbeth Walker, Kissimmee, FL (US)

(*) Notice: Subject to any disclaimer, the term of this patent is extended or adjusted under 35 U.S.C. 154(b) by 240 days.

(21) Appl. No.: 15/597,689

(22) Filed: May 17, 2017

(65) Prior Publication Data

US 2018/0333336 A1   Nov. 22, 2018

(51) Int. Cl.
*A61M 15/00* (2006.01)
*A61M 15/08* (2006.01)
*A61J 17/00* (2006.01)

(52) U.S. Cl.
CPC ............ *A61M 15/00* (2013.01); *A61J 17/006* (2015.05); *A61M 15/08* (2013.01)

(58) Field of Classification Search
CPC .......... A61J 17/001–008; A61M 16/00; A61M 16/10; A62B 7/10; A61L 9/048; A61L 9/013; A61L 9/14
USPC ...................... 128/204.11; 606/234, 235, 236
See application file for complete search history.

(56) References Cited

U.S. PATENT DOCUMENTS

| | | | | |
|---|---|---|---|---|
| 4,032,028 A | * | 6/1977 | Reiss | B65D 50/043 215/217 |
| 5,868,131 A | * | 2/1999 | Murchie | A61M 15/08 128/204.13 |
| 6,557,548 B1 | * | 5/2003 | Dickson | A61M 15/00 128/200.24 |
| 2007/0021783 A1 | * | 1/2007 | Viana | A61M 15/08 606/234 |
| 2016/0058961 A1 | * | 3/2016 | Haas | A61M 15/08 604/94.01 |

* cited by examiner

*Primary Examiner* — Bradley H Philips
*Assistant Examiner* — Vincent D Hoang
(74) *Attorney, Agent, or Firm* — Jason T. Daniel, Esq.; Daniel Law Offices, P.A

(57) ABSTRACT

A decongesting device for infants includes a main body in the form of a child pacifier having a shield and a nipple extending outward from one side thereof. One or more ointment chambers having a body section and a child-resistant cap are permanently or removably secured to the shield on an opposite side of the nipple. The chamber including a hollow interior section for receiving a medicated ointment and a plurality of openings for disseminating vapors produced by the stored ointment. A decongesting device for infants also includes a pacifier body having a shield, a nipple, and a chamber can be pre-filled with a medicated ointment and permanently sealed at a time of manufacture.

9 Claims, 3 Drawing Sheets

DECONGESTING DEVICE FOR INFANTS

TECHNICAL FIELD

The present invention relates generally to the application of decongesting agents, and more particularly to a decongesting device for delivering vapors to the nostrils of an infant.

BACKGROUND

The statements in this section merely provide background information related to the present disclosure and may not constitute prior art.

Historically, infants and children with cold-related ailments such as coughing, congestion, and/or inflammation of the nasal passageways have been treated with body ointments that emanate medicated vapors containing ingredients such as levomenthol, eucalyptus oil, turpentine oil and camphor, for example.

These products are typically layered onto the skin of the child at or about their chest, so as to allow the vapors to be inhaled by the child's nostrils. Unfortunately, it is not uncommon for the child to touch or rub their hand along the ointment, and then subsequently touch their mouth or eyes, causing a good deal of discomfort to child and caregiver alike.

The present invention, directed to a decongesting device for infants differs from the conventional art in a number of aspects. The manner by which will become more apparent in the description which follows, particularly when read in conjunction with the accompanying drawings.

SUMMARY OF THE INVENTION

The present invention is directed to a decongesting device for infants. One embodiment of the present invention can include a main body in the form of a child pacifier having a shield and a nipple extending outward from one side thereof. An ointment chamber having a body section and a child-resistant cap can be secured to the shield on an opposite side of the nipple. The chamber can include a hollow interior section for receiving a medicated ointment and can further include a plurality of openings for disseminating vapors produced by the stored ointment.

One embodiment of the present invention can include a plurality of ointment chambers that are removably secured to the shield.

In one embodiment, the chamber can be pre-filled with a medicated ointment and permanently sealed at a time of manufacture.

This summary is provided merely to introduce certain concepts and not to identify key or essential features of the claimed subject matter.

BRIEF DESCRIPTION OF THE DRAWINGS

Presently preferred embodiments are shown in the drawings. It should be appreciated, however, that the invention is not limited to the precise arrangements and instrumentalities shown.

DETAILED DESCRIPTION OF THE INVENTION

While the specification concludes with claims defining the features of the invention that are regarded as novel, it is believed that the invention will be better understood from a consideration of the description in conjunction with the drawings. As required, detailed embodiments of the present invention are disclosed herein; however, it is to be understood that the disclosed embodiments are merely exemplary of the invention which can be embodied in various forms. Therefore, specific structural and functional details disclosed herein are not to be interpreted as limiting, but merely as a basis for the claims and as a representative basis for teaching one skilled in the art to variously employ the inventive arrangements in virtually any appropriately detailed structure. Further, the terms and phrases used herein are not intended to be limiting but rather to provide an understandable description of the invention.

Although described throughout this document as a device for dispensing medicated vapors to infants, the inventive concepts disclosed herein are not so limiting. In this regard, the below described device can function to store any type of solid or gel products which may or may not have any type of scent. Moreover, the main body can include a shape and size that can be utilized by persons other than children, so as to position the chamber adjacent to the nose of the user.

As described herein, the term "removably secured" and derivatives thereof shall be used to describe a situation wherein two or more objects are joined together in a non-permanent manner so as to allow the same objects to be repeatedly joined and separated. This can be accomplished through the use of any number of commercially available connectors 14 such as opposing strips of hook and loop material (i.e. Velcro®), magnetic elements, and compression fittings such as hooks, snaps and buttons, for example.

Moreover, the term "permanently secured" shall be used to describe a situation wherein two or more objects are joined together in a manner so as to prevent the same objects from being separated. Several nonlimiting examples of suitable connectors for permanently securing items together include adhesives such as glue or resin, hardware such as nuts and bolts, and welds, for example.

Figure 1:
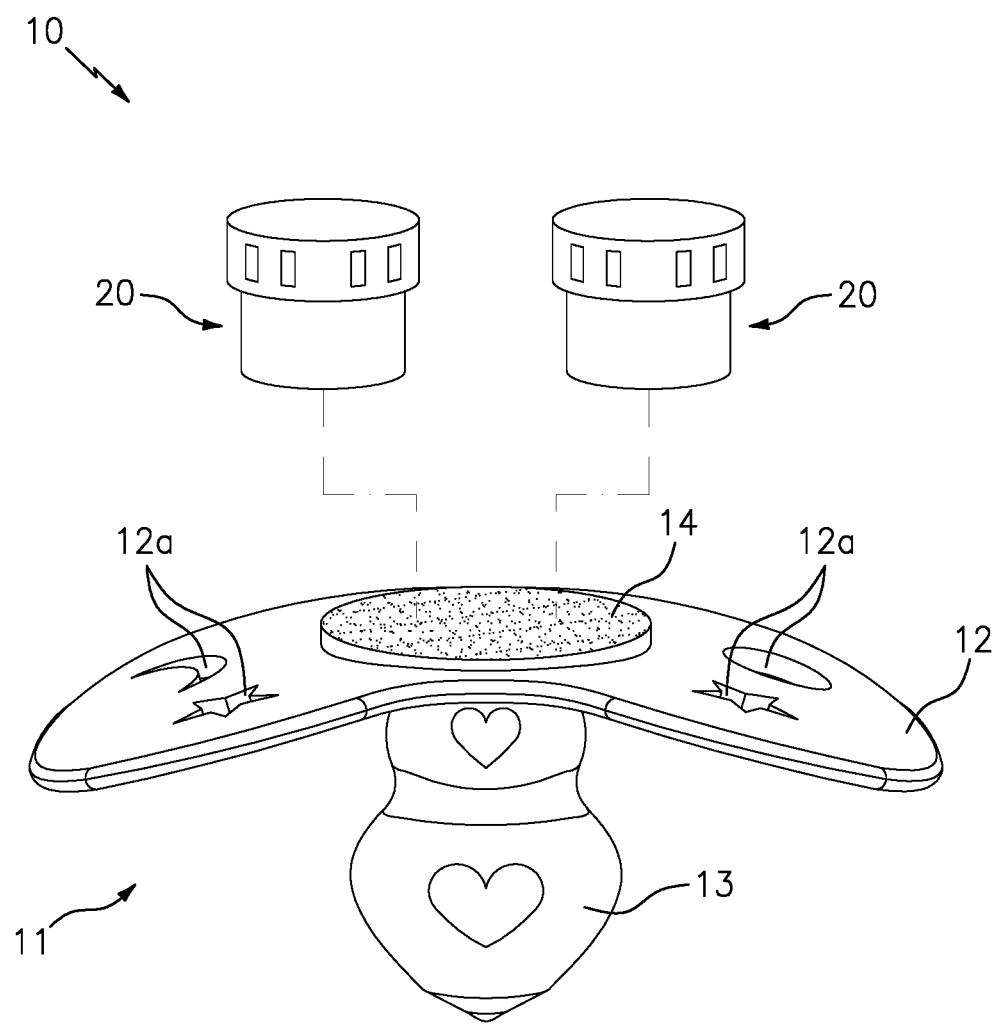
FIG. 1 is an exploded parts view of one embodiment of the decongesting device for infants that is useful for understanding the inventive concepts disclosed herein.
Figure 2:
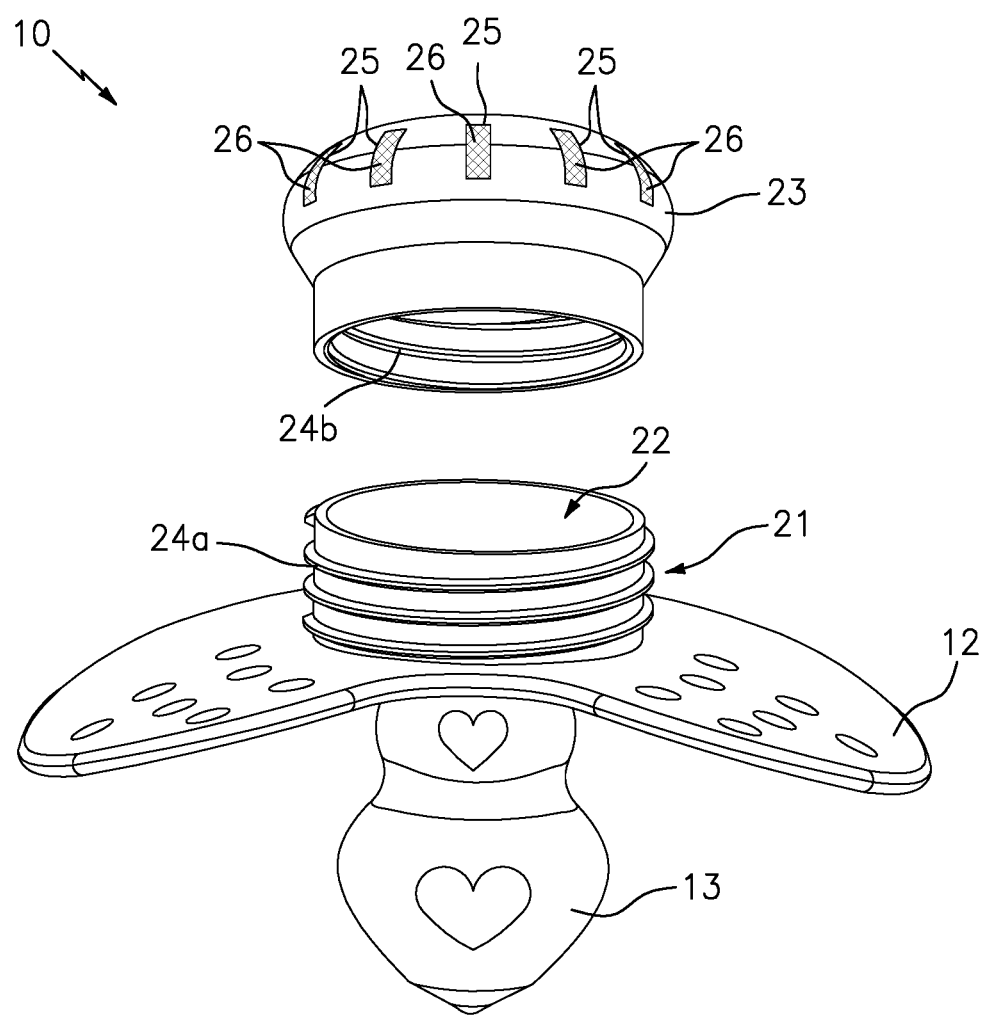
FIG. 2 is side view of the decongesting device for infants, in accordance with one embodiment of the invention.
Figure 3:
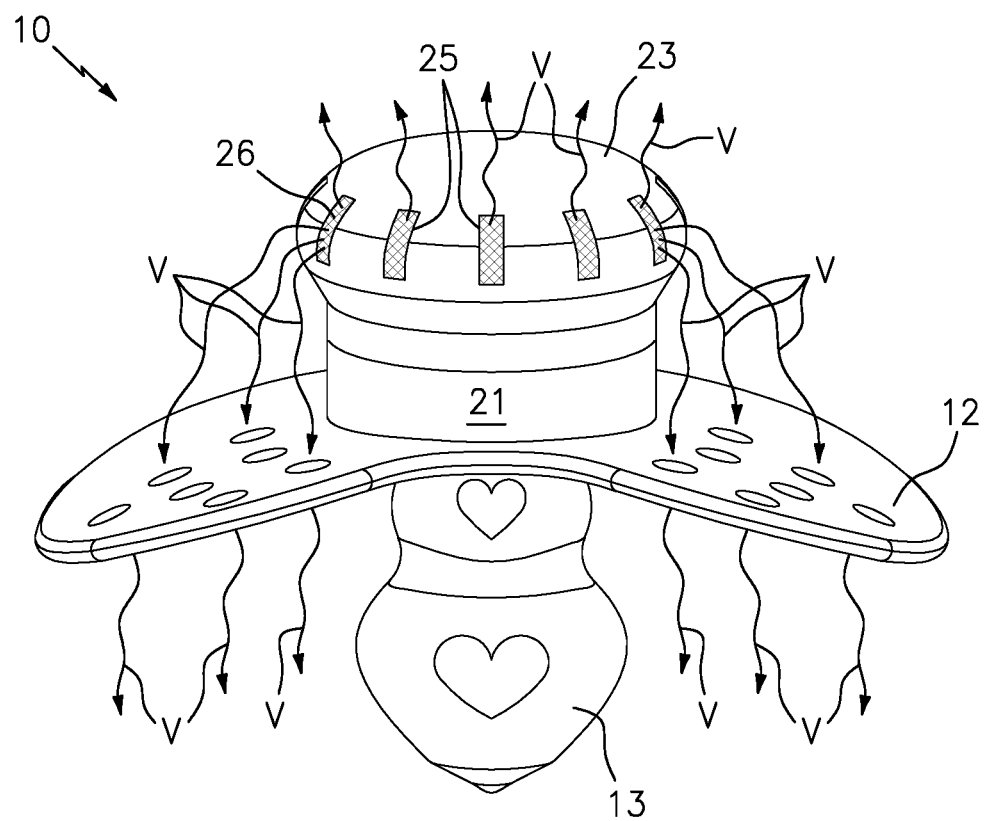
FIG. 3 is another side view of the decongesting device for infants, in accordance with one embodiment of the invention.

FIGS. 1-3 illustrate one embodiment of a decongesting device for infants 10 that are useful for understanding the inventive concepts disclosed herein. In each of the drawings, identical reference numerals are used for like elements of the invention or elements of like function. For the sake of clarity, only those reference numerals are shown in the individual figures which are necessary for the description of the respective figure. For purposes of this description, the terms "upper," "bottom," "right," "left," "front," "vertical," "horizontal," and derivatives thereof shall relate to the invention as oriented in FIG. 1.

As shown in FIG. 1, the device 10 can include a main body 11 in the form of a child's pacifier having a shield member 12, and a nipple 13. One or more ointment chambers 20 can be secured along the main body for storing medicated ointments.

The shield 12 can be constructed from a relatively thin piece of rigid or semi-rigid material such as plastic, for example, that is curved to fit the mouth area of an infant or child. As shown, the shield can include any number of holes 12a to facilitate breathing of the child, and to allow the vapor emanating from the chamber 20 to reach the nose of the child.

The nipple 13 can be suitably attached to one side of the shield 12, and can include any number of different shapes, sizes, and materials such as latex or silicone, for example. The nipple extending longitudinally from the shield 12 in a first direction for insertion into the infant's mouth.

Each ointment chamber 20 can be secured along the shield 12 at an opposite side to that of the nipple 13 via a connector 14. As shown in FIG. 1, such a feature can allow any number of different ointment chambers 20 to be utilized with a single pacifier body 11. This feature advantageously allows a child to utilize the same pacifier both with, and without the medicated ointment. Moreover, parents or guardians can store the chamber(s) separate from the pacifier body, so as to allow the same to be refrigerated and/or to prevent the medicated vapor smell from permeating the pacifier body. Of course, other embodiments are contemplated wherein the bottom portion of the chamber and shield are formed together as an integral component.

In either instance, and as shown best in FIG. 2, each chamber 20 can include a body section in the form of a continuous outer wall 21 that defines a hollow interior space 22 for receiving any number of different ointments. A cap member 23 can be removably secured to the open end of the outer wall via a plurality of threaded elements 24a and 24b. In the preferred embodiment, the combination of the cap 23 and threaded elements 24a and 24b can form a child-resistant safety cap such as that described in U.S. Pat. No. 4,032,028, to Reiss, the contents of which are incorporated herein by reference. Such a feature advantageously functions to prevent a child from accessing the contents of the chamber. Of course, any number of other means for securing the cap to the body in a child-resistant manner are also contemplated.

A plurality of openings 25 can be disposed along the cap member 23 for allowing the vapor from ointment stored within the main body to emanate. In one embodiment, each of the openings can include a mesh lining 26 spanning the opening. The lining can act as a filter that prevents any solid material from escaping the chamber without affecting the vapor.

Although described above with regard to a removable cap for allowing users to refill the chamber with different ointments the inventive concepts are not limiting to such a design. As such, in another embodiment, the cap and body sections of the chamber 20 can be pre-filled with any type of ointment, and permanently sealed by a product manufacturer.

Such a feature may be particularly advantageous in allowing prescription ointments that are produced under the control of the FDA and pharmaceutical companies, to utilize the inventive concepts disclosed herein. In such an instance, a protective outer covering, such as cellophane, for example can be secured about the entire cap section until removed by a patient or caregiver for use by a child.

In either instance, and as shown in FIG. 3, once an ointment is secured within the interior space of the chamber 20, vapor V can escape through the openings 25 of the cap. These vapors can also pass through the holes 12a of the shield 12, for better inhalation by a child that is grasping the nipple with their mouth.

Accordingly, the decongesting device for infants 10 provides a novel solution for allowing a child to inhale any type of medicated vapors without requiring the child to be in physical contact with the vapor producing ointment.

As described herein, one or more elements of the device 10 can be secured together utilizing any number of known attachment means such as, for example, screws, glue, compression fittings and welds, among others. Moreover, although the above embodiments have been described as including separate individual elements, the inventive concepts disclosed herein are not so limiting. To this end, one of skill in the art will recognize that one or more individually identified elements may be formed together as one or more continuous elements, either through manufacturing processes, such as welding, casting, or molding, or through the use of a singular piece of material milled or machined with the aforementioned components forming identifiable sections thereof. As to a further description of the manner and use of the present invention, the same should be apparent from the above description. Accordingly, no further discussion relating to the manner of usage and operation will be provided.

The terminology used herein is for the purpose of describing particular embodiments only and is not intended to be limiting of the invention. As used herein, the singular forms "a," "an," and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. Likewise, the terms "consisting" shall be used to describe only those components identified. In each instance where a device comprises certain elements, it will inherently consist of each of those identified elements as well.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

The invention claimed is:

1. A decongesting device for infants, said device comprising:
   a shield member having a first end, a second end, and a plurality of holes extending therebetween;
   a nipple extending longitudinally outward from the first end of the shield member;
   a chamber that is secured along the second end of the shield member, said chamber including a hollow interior space for storing an ointment;
   a plurality of openings that are positioned along the chamber, said openings functioning to allow vapor produced by the stored ointment to be disseminated to a user; and
   a mesh lining that is disposed across an entirety of each of the plurality of openings along the chamber, said lining being configured to prevent the stored ointment from escaping the chamber.

2. The device of claim 1, wherein the chamber comprises:
a body section having an opening along one end; and
a cap that is removably secured to the body section.

3. The device of claim 1, wherein the chamber comprises:
a body section having an opening along one end; and
a child resistant safety cap that is removably secured to the body section.

4. The device of claim 1, wherein the chamber is removably secured to the second end of the shield member.

5. The device of claim 1, wherein the chamber is permanently secured to the second end of the shield member.

6. The device of claim 1, further comprising:
another chamber that is secured along the second end of the shield member, said another chamber including a hollow interior space for storing another ointment.

7. The device of claim 6, wherein the another chamber comprises a plurality of openings that are positioned along the another chamber, said openings functioning to allow vapor produced by the another ointment to be disseminated to the user.

8. The device of claim 7, wherein the another chamber comprises another mesh lining that is disposed across an entirety of each of the plurality of openings along the another chamber, said another mesh lining being configured to prevent the another ointment from escaping the another chamber.

9. A decongesting device for infants, said device comprising:
a shield member having a first end, a second end, and a plurality of holes extending therebetween;
a nipple extending longitudinally outward from the first end of the shield member;
a sealed chamber that is secured along the second end of the shield member, said sealed chamber including a hollow interior pre-filled with an ointment by a manufacturer of the ointment;
a plurality of openings that are positioned along the chamber, said openings functioning to allow vapor produced by the stored ointment to be disseminated to a user; a mesh lining that is disposed across an entirety of each of the plurality of openings along the chamber, said lining being configured to prevent the stored ointment from escaping the chamber; and
a protective outer covering secured about the sealed chamber.

* * * * *